(12) United States Patent
Paolantonacci et al.

(10) Patent No.: US 10,611,826 B2
(45) Date of Patent: Apr. 7, 2020

(54) AFFINITY CHROMATOGRAPHY MATRIX

(71) Applicant: Laboratoire Français du Fractionnement et des Biotechnologies, Les Ulis (FR)

(72) Inventors: Philippe Paolantonacci, Gif sur Yvette (FR); Abdessatar Chtourou, Elancourt (FR)

(73) Assignee: Laboratoire Français du Fractionnement et des Biotechnologies, Les Ulis (FR)

( * ) Notice: Subject to any disclaimer, the term of this patent is extended or adjusted under 35 U.S.C. 154(b) by 850 days.

(21) Appl. No.: 14/902,716

(22) PCT Filed: Jul. 4, 2014

(86) PCT No.: PCT/FR2014/051734
§ 371 (c)(1),
(2) Date: Jan. 4, 2016

(87) PCT Pub. No.: WO2015/001277
PCT Pub. Date: Jan. 8, 2015

(65) Prior Publication Data
US 2016/0168229 A1 Jun. 16, 2016

(30) Foreign Application Priority Data

Jul. 5, 2013 (FR) .................................. 13 56635
Jul. 5, 2013 (FR) .................................. 13 56636

(51) Int. Cl.
*C07K 16/06* (2006.01)
*C07K 1/22* (2006.01)
(Continued)

(52) U.S. Cl.
CPC ...... *C07K 16/065* (2013.01); *A61K 39/39525* (2013.01); *B01D 15/3804* (2013.01);
(Continued)

(58) Field of Classification Search
CPC ........ C07K 16/065; C07K 16/34; C07K 1/22; B01J 20/291; B01J 20/265; B01J 2220/80; B01D 15/3809
(Continued)

(56) References Cited

U.S. PATENT DOCUMENTS 3,519,558 A   7/1970   Cooper et al.
3,757,005 A   9/1973   Kautz et al.
(Continued)

FOREIGN PATENT DOCUMENTS

AU   2006334278 B2   7/2007
AU   2013200440 A1   2/2013
(Continued)

OTHER PUBLICATIONS

Cohen et al., Preparation and Properties of Serum and Plasma Proteins. IV. A System for the Separation into Fractions of the Protein and Lipoprotein Components of Biological Tissues and Fluids[1,a,b,c,d] J Am Chem Soc. Mar. 1946;68:459-75.
(Continued)

*Primary Examiner* — Vishal V Vasisth
(74) *Attorney, Agent, or Firm* — Wolf, Greenfield & Sacks, P.C.

(57) ABSTRACT

The invention relates to an affinity chromatography matrix, as a gel, comprising polymeric particles on which at least one oligosaccharide corresponding to a blood group A epitope and/or blood group B is grafted, via a spacer, characterized in that the density of oligosaccharides is comprised between 0.2 and 0.7 mg/ml of matrix. The invention also relates to the uses of this matrix for preparing concentrates of immunoglobulins for therapeutic use.

17 Claims, 2 Drawing Sheets

(51) Int. Cl.
*B01J 20/32* (2006.01)
*B01J 20/289* (2006.01)
*A61K 39/395* (2006.01)
*B01D 15/38* (2006.01)
*B01J 20/26* (2006.01)
*B01J 20/291* (2006.01)
*C07K 16/34* (2006.01)

(52) U.S. Cl.
CPC ........ *B01D 15/3809* (2013.01); *B01J 20/265* (2013.01); *B01J 20/289* (2013.01); *B01J 20/291* (2013.01); *B01J 20/3219* (2013.01); *B01J 20/3251* (2013.01); *B01J 20/3255* (2013.01); *B01J 20/3274* (2013.01); *C07K 1/22* (2013.01); *C07K 16/34* (2013.01); *B01J 2220/80* (2013.01); *Y02P 20/582* (2015.11)

(58) Field of Classification Search
USPC .................. 530/387.5; 252/184; 536/17.9
See application file for complete search history.

(56) References Cited

U.S. PATENT DOCUMENTS

| | | |
|---|---|---|
| 4,089,778 A | 5/1978 | Gauger |
| 4,105,547 A | 8/1978 | Sandblom et al. |
| 4,350,156 A | 9/1982 | Malchesky et al. |
| 4,351,710 A | 9/1982 | Jain et al. |
| 4,397,747 A | 8/1983 | Ikeda |
| 4,420,398 A | 12/1983 | Castino |
| 4,764,369 A | 8/1988 | Neurath et al. |
| 4,789,482 A | 12/1988 | Dileo et al. |
| 4,888,115 A | 12/1989 | Marinaccio et al. |
| 4,971,670 A | 4/1990 | Faupel et al. |
| 5,256,294 A | 10/1993 | van Reis et al. |
| 5,490,937 A | 2/1996 | van Reis et al. |
| 5,518,624 A | 5/1996 | Filson et al. |
| 5,576,040 A | 11/1996 | Moller et al. |
| 5,597,486 A | 1/1997 | Lutz |
| 5,648,253 A | 7/1997 | Wei |
| 5,756,687 A | 5/1998 | Denman et al. |
| 5,827,690 A | 10/1998 | Meade et al. |
| 5,843,705 A | 12/1998 | DiTullio et al. |
| 5,849,992 A | 12/1998 | Meade et al. |
| 5,948,441 A | 9/1999 | Lenk et al. |
| 6,054,051 A | 4/2000 | van Reis et al. |
| 6,194,553 B1 | 2/2001 | Lee et al. |
| 6,210,736 B1 | 4/2001 | Echelard et al. |
| 6,221,249 B1 | 4/2001 | van Reis et al. |
| 6,268,487 B1 | 7/2001 | Kutzko et al. |
| 6,387,270 B1 | 5/2002 | van Reis et al. |
| 6,441,145 B1 | 8/2002 | DiTullio et al. |
| 6,448,469 B1 | 9/2002 | Smith |
| 6,472,584 B1 | 10/2002 | Smith |
| 6,528,699 B1 | 3/2003 | Meade et al. |
| 6,545,198 B1 | 4/2003 | Echelard et al. |
| 6,548,653 B1 | 4/2003 | Young et al. |
| 6,555,006 B2 | 4/2003 | van Reis et al. |
| 6,580,017 B1 | 6/2003 | Echelard et al. |
| 6,593,463 B1 | 7/2003 | Chen et al. |
| 6,727,405 B1 | 4/2004 | Gordon et al. |
| 6,743,966 B2 | 6/2004 | Smith |
| 6,870,034 B2 | 3/2005 | Breece et al. |
| 7,019,193 B2 | 3/2006 | Ditullio et al. |
| 7,045,676 B1 | 5/2006 | Gordon et al. |
| 7,087,719 B2 | 8/2006 | Visuri et al. |
| 7,101,971 B2 | 9/2006 | Meade et al. |
| 7,354,594 B2 | 4/2008 | Chen et al. |
| 7,501,553 B2 | 3/2009 | Chen et al. |
| 7,531,632 B2 | 5/2009 | Perreault |
| 7,550,263 B2 | 6/2009 | Meade et al. |
| 7,632,980 B1 | 12/2009 | Chen et al. |
| 7,651,686 B2 | 1/2010 | Chen et al. |
| 7,928,064 B2 | 4/2011 | DiTullio et al. |
| 7,939,317 B1 | 5/2011 | Gordon et al. |
| 8,173,860 B2 | 5/2012 | Meade et al. |
| 9,511,087 B2 | 12/2016 | Frieling et al. |
| 10,034,921 B2 | 7/2018 | Chen et al. |
| 10,174,110 B2 | 1/2019 | Meade et al. |
| 2002/0108907 A1 | 4/2002 | van Reis et al. |
| 2002/0131957 A1 | 9/2002 | Gavin et al. |
| 2002/0144299 A1 | 10/2002 | Chen et al. |
| 2002/0155998 A1 | 10/2002 | Young et al. |
| 2003/0005468 A1 | 1/2003 | Meade et al. |
| 2003/0033618 A1 | 2/2003 | Smith |
| 2003/0036637 A1 | 2/2003 | Fulton |
| 2003/0046716 A1 | 3/2003 | Echelard et al. |
| 2003/0096974 A1 | 5/2003 | Ditullio et al. |
| 2003/0177513 A1 | 9/2003 | Echelard et al. |
| 2003/0178367 A1 | 9/2003 | van Reis et al. |
| 2003/0204860 A1 | 10/2003 | Melican et al. |
| 2003/0213003 A1 | 11/2003 | Meade et al. |
| 2003/0229212 A1 | 12/2003 | Fahrner et al. |
| 2004/0006776 A1 | 1/2004 | Meade et al. |
| 2004/0025193 A1 | 2/2004 | Echelard et al. |
| 2004/0092719 A1 | 5/2004 | Birck-Wilson et al. |
| 2004/0097710 A1 | 5/2004 | Visuri et al. |
| 2004/0098755 A1 | 5/2004 | Mulroy et al. |
| 2004/0102380 A1 | 5/2004 | Fulton et al. |
| 2004/0109847 A1 | 6/2004 | Chen et al. |
| 2004/0117863 A1 | 6/2004 | Edge et al. |
| 2004/0121303 A1 | 6/2004 | Gavin et al. |
| 2004/0133931 A1 | 7/2004 | Gavin et al. |
| 2004/0143857 A1 | 7/2004 | Young et al. |
| 2004/0148648 A1 | 7/2004 | Behboodi et al. |
| 2004/0167320 A1 | 8/2004 | Couto et al. |
| 2004/0171103 A1 | 9/2004 | Bradley et al. |
| 2004/0192595 A1 | 9/2004 | Murakami et al. |
| 2004/0205832 A1 | 10/2004 | Meade et al. |
| 2004/0226052 A1 | 11/2004 | Meade et al. |
| 2004/0226053 A1 | 11/2004 | Meade et al. |
| 2004/0242857 A1 | 12/2004 | Nilsson |
| 2005/0013811 A1 | 1/2005 | Chen et al. |
| 2005/0029195 A1 | 2/2005 | Gibson et al. |
| 2005/0060766 A1 | 3/2005 | Chen |
| 2005/0071890 A1 | 3/2005 | Chen et al. |
| 2005/0097625 A1 | 5/2005 | Meade et al. |
| 2005/0158832 A1 | 7/2005 | Young et al. |
| 2005/0160483 A1 | 7/2005 | Meade et al. |
| 2005/0169908 A1 | 8/2005 | Murakami et al. |
| 2005/0177882 A1 | 8/2005 | Gavin et al. |
| 2005/0181482 A1 | 8/2005 | Meade et al. |
| 2005/0186608 A1 | 8/2005 | Olsen |
| 2005/0192226 A1 | 9/2005 | Enkhbaatar et al. |
| 2005/0193431 A1 | 9/2005 | Echelard et al. |
| 2005/0197496 A1 | 9/2005 | Perreault |
| 2005/0208000 A1 | 9/2005 | Bernstein et al. |
| 2005/0235371 A1 | 10/2005 | Chen et al. |
| 2005/0245444 A1 | 11/2005 | Echelard et al. |
| 2005/0260672 A1 | 11/2005 | Couto et al. |
| 2006/0026695 A1 | 2/2006 | Edge et al. |
| 2006/0105347 A1 | 5/2006 | Meade et al. |
| 2006/0121004 A1 | 6/2006 | Echelard et al. |
| 2006/0123500 A1 | 6/2006 | Echelard et al. |
| 2006/0130159 A1 | 6/2006 | Masiello et al. |
| 2006/0168671 A1 | 7/2006 | Gavin et al. |
| 2006/0174359 A1 | 8/2006 | Melican et al. |
| 2006/0178309 A1 | 8/2006 | Visuri et al. |
| 2006/0179493 A1 | 8/2006 | Meade et al. |
| 2006/0179500 A1 | 8/2006 | Meade et al. |
| 2006/0182744 A1 | 8/2006 | Strome et al. |
| 2006/0191025 A1 | 8/2006 | Echelard et al. |
| 2006/0191029 A1 | 8/2006 | Gavin et al. |
| 2006/0286548 A1 | 12/2006 | Liposky et al. |
| 2007/0037192 A1 | 2/2007 | Ziomek et al. |
| 2007/0192878 A1 | 8/2007 | Perreault |
| 2008/0004212 A1 | 1/2008 | Echelard et al. |
| 2008/0019905 A9 | 1/2008 | Strome et al. |
| 2008/0063780 A1 | 3/2008 | Meade et al. |
| 2008/0118501 A1 | 5/2008 | Schindler et al. |
| 2008/0176786 A1 | 7/2008 | Ditullio et al. |
| 2008/0207487 A1 | 8/2008 | DeFrees et al. |
| 2009/0068193 A1 | 3/2009 | Chen et al. |
| 2009/0246194 A1 | 10/2009 | Meade et al. |

(56) References Cited

U.S. PATENT DOCUMENTS

| | | |
|---|---|---|
| 2010/0021612 A1 | 1/2010 | Meade et al. |
| 2010/0047428 A1 | 2/2010 | Lejars et al. |
| 2010/0056757 A1 | 3/2010 | Perreault |
| 2011/0070167 A1 | 3/2011 | Enkhbaatar et al. |
| 2011/0082083 A1 | 4/2011 | Magneson et al. |
| 2011/0229460 A1 | 9/2011 | Meade |
| 2012/0058047 A9 | 3/2012 | Strome et al. |
| 2013/0149301 A1 | 6/2013 | Meade |
| 2013/0324619 A1 | 12/2013 | Chtourou |
| 2014/0046033 A1 | 2/2014 | Schindler et al. |
| 2014/0194360 A1 | 7/2014 | Frieling et al. |
| 2014/0206617 A1 | 7/2014 | Frieling et al. |
| 2014/0228301 A1 | 8/2014 | Meade et al. |
| 2014/0242182 A1 | 8/2014 | Evans et al. |
| 2014/0296490 A1 | 10/2014 | Faid et al. |
| 2015/0368334 A1 | 12/2015 | Meade et al. |
| 2015/0368357 A1 | 12/2015 | Meade et al. |
| 2015/0374801 A1 | 12/2015 | Chen et al. |
| 2016/0002330 A1 | 1/2016 | Meade |
| 2016/0039913 A1 | 2/2016 | Meade et al. |
| 2016/0089422 A1 | 3/2016 | Chtourou et al. |
| 2016/0129115 A1 | 5/2016 | Magneson et al. |
| 2016/0158676 A1 | 6/2016 | Hawkins et al. |
| 2016/0168229 A1 | 6/2016 | Paolantonacci et al. |
| 2016/0326547 A1 | 11/2016 | Meade et al. |
| 2017/0121402 A1 | 5/2017 | Chtourou |
| 2017/0129966 A1 | 5/2017 | Masiello |
| 2017/0190753 A1 | 7/2017 | Abache |
| 2018/0139938 A1 | 5/2018 | Chen |
| 2018/0169297 A1 | 6/2018 | Chtourou et al. |
| 2018/0355034 A1 | 12/2018 | Mondon et al. |
| 2019/0254276 A1 | 8/2019 | Chtourou |

FOREIGN PATENT DOCUMENTS

| | | |
|---|---|---|
| CA | 2 634 997 A1 | 12/2007 |
| CN | 1387399 A | 12/2002 |
| EP | 0320472 A1 | 6/1989 |
| EP | 0 552 192 | 3/1995 |
| EP | 2556848 A1 | 2/2013 |
| GB | 2178742 | 2/1987 |
| JP | 2008-543868 A | 12/2008 |
| JP | 2009-521520 A | 6/2009 |
| WO | WO 85/03011 | 7/1985 |
| WO | WO 92/04970 | 4/1992 |
| WO | WO 94/29334 A1 | 12/1994 |
| WO | WO 99/64462 A1 | 12/1999 |
| WO | WO 00/48703 | 8/2000 |
| WO | WO 01/26455 A1 | 4/2001 |
| WO | WO 02/30954 A1 | 4/2002 |
| WO | WO 2002/092632 | 11/2002 |
| WO | WO 03/045996 A1 | 6/2003 |
| WO | WO 2005/044856 A2 | 5/2005 |
| WO | WO 2006/138553 A2 | 12/2006 |
| WO | WO 2007/077365 A2 | 7/2007 |
| WO | WO 2010/030393 A1 | 3/2010 |
| WO | WO 2013/066251 A1 | 5/2013 |
| WO | WO 2014/140927 A2 | 9/2014 |
| WO | WO 2015/186004 A2 | 12/2015 |

OTHER PUBLICATIONS

Oncley et al., The Separation of the Antibodies, Isoagglutinins, Prothrombin, Plasminogen and $\beta_1$-Lipoprotein into Subfractions of Human Plasma. J Am Chem Soc. Feb. 1949;71(2):541-50.

Steinbuch et al. The isolation of IgG from mammalian sera with the aid of caprylic acid. Arch Biochem Biophys. Nov. 1969;134(2):279-84.

Thorpe et al., International collaborative study to evaluate candidate reference reagents to standardize haemagglutination testing for anti-A and anti-B in normal intravenous immunoglobulin products. Vox Sang. Aug. 2009;97(2):160-8. doi: 10.1111/j.1423-0410.2009.01194.x. Epub Apr. 27, 2009.

Baruah et al., Purification of monoclonal antibodies derived from transgenic goat milk by ultrafiltration. Biotechnol Bioeng. Mar. 5, 2006;93(4):747-54.

Borneman et al., Semi-continuous protein fractionating using Affinity Cross-Flow Filtration. Desalination 144 (2002) 295-299.

Chakravarti et al., Current Protocols in Essential Laboratory Techniques. Unit 6.2: Column Chromatography. 2008; John Wiley & Sons, Inc: 6.2.1-6.2.14.

Cheryan, Ultrafiltration handbook: Introduction and Definition and Classification of Membrane Separation Process. Technomic Publishing Co., Inc. Dec. 1987;38(12):2-5.

Christy et al., (2002) High Performance Tangential Flow Filtration: A Highly Selective Membrane Separation Process, Desalination, vol. 144: 133-36.

De Jonge et al., (1993), Filtration Processes in the Cohn Fractionation Process. Biotechnol Blood Proteins, 227:49-54.

Denman et al., Transgenic expression of a variant of human tissue-type plasminogen activator in goat milk: purification and characterization of the recombinant enzyme. Biotechnology (NY). Sep. 1991;9(9):839-43.

Du et al., An integrated expanded bed adsorption process for lactoferrin and immunoglobulin G purification from crude sweet whey. J Chromatogr B Analyt Technol Biomed Life Sci. Feb. 1, 2014;947-948:201-7. doi: 10.1016/j.jchromb.2013.12.020. Epub Dec. 27, 2013.

Guerrier et al., A dual-mode approach to the selective separation of antibodies and their fragments. J Chromatogr B Biomed Sci Appl. May 5, 2001;755(1-2):37-46.

Ha et al., Isolation and characterization of IgG1 with asymmetrical Fc glycosylation. Glycobiology. Aug. 2011;21(8):1087-96. doi: 10.1093/glycob/cwr047. Epub Apr. 5, 2011.

Labrou, Protein purification: an overview. Methods Mol Biol. 2014;1129:3-10. doi: 10.1007/978-1-62703-977-2_1.

Millesime et al., (1996) Fractionation of Proteins with Modified Membranes, Bioseparation, Jun;6(3):135-45.

Olson et al. Separations Technology: Pharmaceutical and Biotechnology Applications: Tangential Flow Filtration, Application Classes in Pharmaceutical Separations. Editor Wayne P. Olson, Interpharm Press, Inc, Buffalo Grove, IL. 1995:126-135.

Prado et al., (1999), Development and Validation Study for the Chromatographic Purification Process for Tetanus Anatoxin on Sephacryl S-200 High Resolution, Boll Chem Farm. 138(7):364-368.

Sadavarte et al., Purification of chimeric heavy chain monoclonal antibody EG2-hFc using hydrophobic interaction membrane chromatography: an alternative to protein-A affinity chromatography. Biotechnol Bioeng. Jun. 2014;111(6):1139-49. doi: 10.1002/bit.25193. Epub Feb. 17, 2014.

Valliere-Douglass et al., Separation of populations of antibody variants by fine tuning of hydrophobic-interaction chromatography operating conditions. J Chromatogr A. Dec. 19, 2008;1214(1-2):81-9. doi: 10.1016/j.chroma.2008.10.078. Epub Oct. 25, 2008.

Van Reis et al., High Performance Tangential Flow Filtration, Biotech. Bioeng., 56: 71-82, (1997).

Van Reis et al., Membrane Separations in Biotechnology, Curr Opin Biotechnol., Apr. 2001; 12(2):208-11.

Yang et al., Recombinant Human Antithrombin Expressed in the Milk of Non-Transfenic Goats Exhibits High Efficiency on Rat Dic Model. J Thromb Thrombolysis. 2009;28;449-457.

Zeman et al., Principles and Applications: Microfiltration and Ultrafiltration: Basic Chemistry and Physics of MF/UF Membranes. Marcel Dekker, Inc., New York. Jul. 9, 1996:p. 11.

ns G (IgG) for therapeutic use.

AFFINITY CHROMATOGRAPHY MATRIX

RELATED APPLICATIONS

This application is a national stage filing under 35 U.S.C. § 371 of International Application No. PCT/FR2014/051734, filed Jul. 4, 2014, entitled "Affinity Chromatography Matrix," and which claims priority to FR 1356635, filed Jul. 5 2013 and FR 1356636, filed Jul. 5, 2013, the entire contents of each of which is herein incorporated by reference in its entirety.

The present invention relates to a matrix for applying affinity chromatography, intended to retain and remove antibodies directed against antigens of the blood group A and/or of the blood group B, of a blood product.

TECHNOLOGICAL BACKGROUND

Many pathologies are presently treated with compositions of immunoglobulins (Ig). For example mention may be made of primitive immunodeficiencies with a lack of production of antibodies, Kawasaki's disease, immune thrombopenic purpura of children and adults, secondary immunodeficiencies with lack of production of antibodies, notably chronic lymphoid leukemia or a myeloma associated with recurrent infections, infection of children with the HIV associated with bacterial infections, multifocal motor neuropathies, Guillain-Barre's syndrome, severe or chronic acute infections with Parvovirus B19, acquired or constitutive immunodeficiency, cortico-resistant dermatomyositis, acute myasthenia, idiopathic chronic polyradiculoneuritis, immune thrombopenic purpura, for example associated with HIV infection, Stiffman syndrome, auto-immune neutropenia, resistant auto-immune erythroblastopenia, anti-coagulation syndrome acquired by auto-antibodies, rheumatoid polyarthritis, uveitises, etc.

The increasing use of human plasma fractions enriched in Ig in therapy requires large scale production, for example from human plasmas, of highly purified Ig concentrates, injectable via an intravenous route (IgIV), or sub-cutaneous route (Igsc).

Now this production is confronted with many constraints, notably in terms of innocuousness of the obtained Ig concentrates.

According to European Pharmacopeia, in order to reduce the risks of hemolysis, these concentrates should have a reduced content of antibodies directed against the antigens of the blood group A and/or of the blood group B (designated in the description in an abbreviated way, as "anti-blood group A antibody" and "anti-blood group B", or further "anti-A antibody" and "anti-B antibody", or further "anti-A isoagglutinins" and "anti-B isoagglutinins").

Given that the needs in Ig are constantly increasing, it is necessary to have increasingly large pools of donors, which will be statistically richer in blood group O. Therefore it has become essential to have processes giving the possibility of removing the anti-A and anti-B antibodies of blood products, during the industrial production of Ig concentrates from pools of blood plasmas.

Application WO2007/077365 describes a process for preparing Ig concentrates, comprising an immunoaffinity chromatography step aiming at depleting the latter in anti-A and anti-B antibodies.

SUMMARY OF THE INVENTION

The Applicant has now developed a support, particularly useful for retaining, and removing anti-A and/or anti-B antibodies of a blood product, by affinity chromatography on an industrial scale.

The invention thus provides an affinity chromatography matrix, as a gel, comprising polymeric particles on which at least one oligosaccharide corresponding to a blood group A and/or group B epitope is grafted, said oligosaccharide being grafted to said particles via a spacer, characterized in that the density of oligosaccharides is comprised between 0.2 and 0.7 mg/ml of matrix. Said spacer is characterized in that it has formula (I) —NH—R1-CO—NH—R2, wherein R1 is a $C_4$-$C_6$ alkyl group, R2 is a $C^3$-$C_8$ alkyl group, and said spacer is bound through its amine function to the particle. A diagram of these grafted particles is shown in FIG. 1.

In a particular embodiment, the matrix comprises (i) polymeric particles on which at least one oligosaccharide corresponding to a blood group A epitope is grafted, and/or (ii) polymeric particles on which at least one oligosaccharide corresponding to a blood group B epitope is grafted.

In a preferred embodiment, the matrix comprises (i) polymeric particles on which at least one oligosaccharide corresponding to a blood group A epitope is grafted, and (ii) polymeric particles on which at least one oligosaccharide corresponding to a blood group B epitope is grafted. This embodiment is illustrated in FIG. 4A.

In another embodiment, the matrix comprises polymeric particles on which both at least one oligosaccharide corresponding to a blood group A epitope and at least one oligosaccharide corresponding to a blood group B epitope, are grafted. This embodiment is illustrated in FIG. 4B.

In a particular embodiment, the matrix comprises a mixture of (i) polymeric particles on which at least one oligosaccharide corresponding to a blood group A epitope is grafted, (ii) of polymeric particles on which at least one oligosaccharide corresponding to a blood group B epitope is grafted, and (iii) of polymeric particles on which both at least one oligosaccharide corresponding to a blood group A epitope and at least one oligosaccharide corresponding to a blood group B epitope, are grafted. This embodiment is illustrated in FIG. 4C.

In all the embodiments, the spacer which binds the ligand corresponding to a blood group A epitope to the particle, and the spacer which binds the ligand corresponding to a blood group B epitope to the particle may be identical or different, preferably identical, but always with formula (I).

The invention further aims at the use of this matrix, or support, in affinity chromatography binding anti-A and/or anti-B antibodies.

The invention also aims at the use of this matrix, or support, for producing on an industrial scale, immunoglobulins G (IgG) for therapeutic use.

The invention also provides a process for preparing a concentrate of immunoglobulins (Ig) for therapeutic use, comprising obtaining of an Ig composition from blood plasma, by ethanol fractionation and/or caprylic fractionation and/or chromatographic separation, and removing the anti-A and/or anti-B antibodies possibly present in the composition, by means of an affinity chromatography using the matrix as defined here.

An advantage of this matrix is its high selectivity and specificity towards anti-A and anti-B antibodies, and its high binding capacity to the latter. Therefore, it becomes possible to reduce the treatment time of products on an industrial scale, by letting through a larger amount of products per column volume.

LEGENDS TO THE FIGURES

Figure 4A:
FIG. 4A represents a simplified diagram of a particular embodiment of the invention, of a matrix comprising a mixture of particles bearing an oligosaccharide corresponding to a blood group A epitope, and of particles bearing an oligosaccharide corresponding to a blood group B epitope.
Figure 4B:
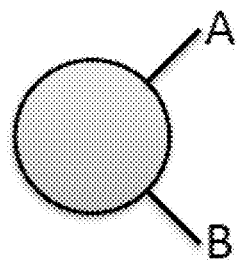
FIG. 4B illustrates a simplified diagram of a particular embodiment of the invention, of a matrix comprising particles both bearing an oligosaccharide corresponding to a blood group A epitope and an oligosaccharide corresponding to a blood group B epitope.
Figure 4C:
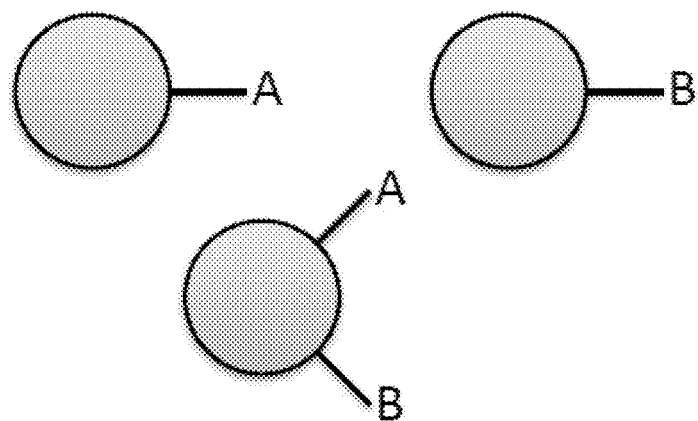

FIG. 4C illustrates a simplified diagram of a particular embodiment of the invention, of a matrix comprising a mixture of particles bearing an oligosaccharide corresponding to a blood group A epitope, of particles bearing an oligosaccharide corresponding to a blood group B epitope, and particles both bearing an oligosaccharide corresponding to a blood group A epitope and an oligosaccharide corresponding to a blood group B epitope.

DETAILED DESCRIPTION OF THE INVENTION

The Support:

The matrix of the invention comprises a support of polymeric particles, and is preferably in the form of a gel or of a resin.

These polymeric particles are preferably of spherical or oblong shape, these may notably be beads. These particles generally have an average size of about 0.1 μm to about 1,000 μm, preferably from about 20 to about 500 μm, still preferably from about 50 to about 200 μm, still preferably from about 70 μm to about 120 μm in diameter.

Preferably these particles are porous.

The polymer may be natural or nonnatural, organic or inorganic, cross-linked or not crosslinked.

The polymer is preferably an organic polymer, preferably cross-linked.

In a preferred embodiment, the polymer is cellulose, and the particles are preferably porous cellulose beads.

Still preferably, this is cross-linked cellulose.

Other types of possible polymers include agarose, dextran, polyacrylates, polystyrene, polyacrylamide, polymethacrylamide, copolymers of styrene and divinylbenzene, or mixtures of these polymers.

The particles may provide a chromatography medium which may be used for filling a column for example.

The Ligands:

The ligands borne by the support according to the invention are oligosaccharides representing the antigens of the blood groups A or B, which are naturally ores.

More specifically, the oligosaccharide corresponding to a blood group A epitope and/or the oligosaccharide corresponding to a blood group B epitope borne by the matrix according to the invention are typically trisaccharides. The term "oligosaccharides corresponding to a blood group epitope" refers to identical or similar units, from an antigen point of view, with the antigenic determinants recognized by the anti-A and anti-B antibodies, respectively. The ligands borne by the support according to the invention are therefore specific to anti-A or anti-B antibodies.

Preferably, the oligosaccharide corresponding to a blood group A epitope, used as a ligand in the invention, is a trisaccharide, N-acetylgalactosamine (GalNAc)-Galactose (Gal)-Fucose, more specifically N-acetylGalα1-3(Fuc α1-2) Gal, the spacer is bound through the oxygen atom preferably bound to the carbon in position 1 of the galactose:

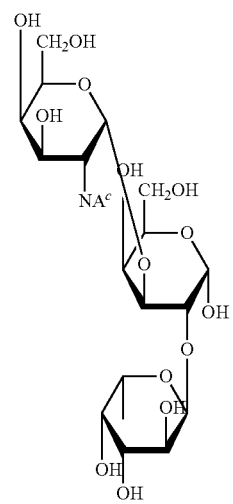

The oligosaccharide corresponding to a blood group B epitope, used as a ligand in the invention is preferably an oligosaccharide, Galactose-Galactose-Fucose, more specifically Gal α1-3(Fuc α1-2)Gal, the spacer is bound to the oxygen atom preferably bound to the carbon in position 1 of the galactose:

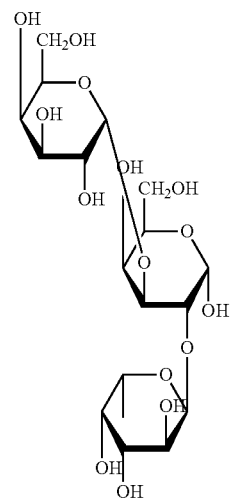

The Spacer:

The ligand is bound covalently to the spacer, which binds the ligand to the particles. The spacer gives the possibility of reducing the steric hindrance and increasing accessibility of the ligand towards anti-A and anti-B antibodies to bind.

The spacer is used for immobilizing, on a particle, either an oligosaccharide corresponding to a blood group A epitope, which is preferably a trisaccharide, N-acetylGalα1-

3(Fuc α1-2)Gal as described above, or an oligosaccharide corresponding to a blood group B epitope, which preferably is a trisaccharide, Galα1-3(Fuc α1-2)Gal, as described above.

A particle may bear several spacers.

The bond between the ligand and the spacer may for example be an amide bond.

The spacer typically comprises at least one C, O, N, or S atom.

It may for example be $-(CH_2)_mX(CH_2)_n-$ or $-(CH_2)_mX1(CH_2)_nX2(CH_2)_p-$, wherein X, X1, and X2 are each independently of each other selected from O, S, NH, and a covalent bond; and m, n, and p are each independently 0, 1, 2, 3, 4, 5, or 6. In another embodiment, 1, 2, or 3 of the hydrogen atoms above may be replaced by an equivalent number of OH and/or methyl groups.

In an embodiment, the spacer comprises a structure selected from

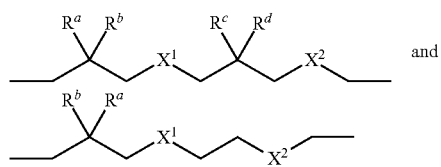

wherein each of X1 and X2 is selected independently from O, S, and NH; and each of Ra, Rb, Rc, and Rd is selected independently from H, OH, and methyl.

In another embodiment, the spacer comprises a structure selected from among

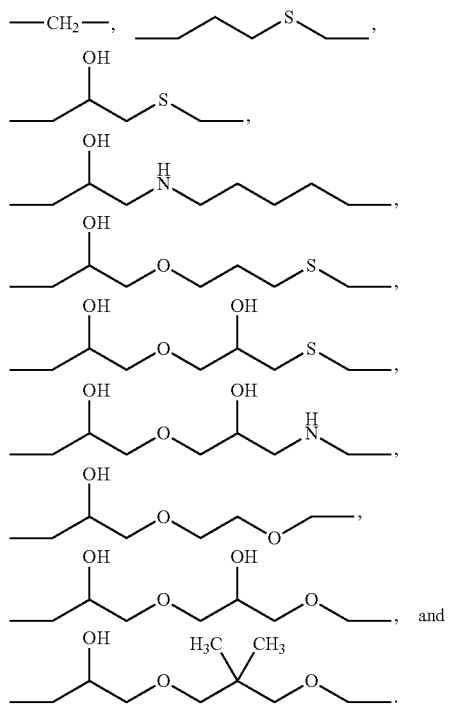

Figure 1:
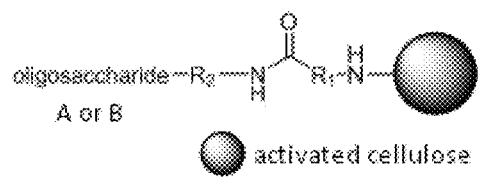
FIG. 1 illustrates a simplified diagram of a polymeric particle on which one oligosaccharide corresponding to a blood group A or B epitope is grafted, in a particular embodiment according to the invention.

In a preferred embodiment, the spacer has the formula (I) —NH—R1—CO—NH—R2-, wherein R1 is a $C_4$-$C_6$ alkyl group, R2 is a $C_3$-$C_8$ alkyl group, and said spacer is bound through its amine function to the particle (in bold characters above). A diagram of this matrix is shown in FIG. 1.

R1 is a linear or branched, preferably linear, $C_4$-$C_6$ alkyl group. Preferably, R1 is a $C_5$ alkyl group.

R2 is a linear or branched, preferably linear, $C_3C_8$ alkyl group. Preferably, R2 is a $C_3$ alkyl group.

In a preferred embodiment, the ligands (which preferably are trisaccharides as described above) are grafted to the particles with a spacer of formula: (particle)-NH—$C_5H_{10}$—CO—NH—$C_3H_6$-(ligand).

Figure 2:
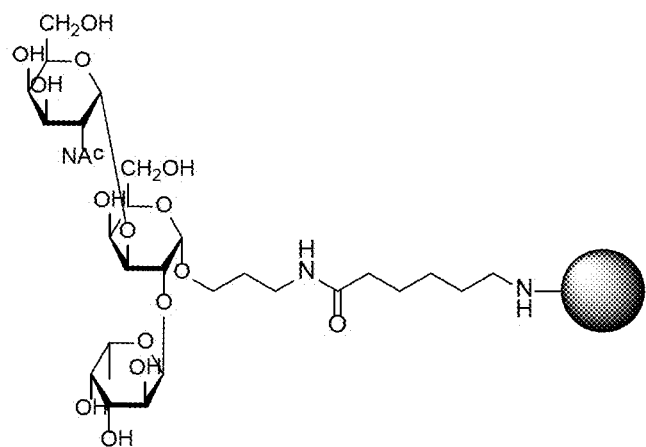
FIG. 2 illustrates a simplified diagram of a preferred embodiment of the invention, illustrating a polymeric particle on which a trisaccharide corresponding to a blood group A epitope is grafted.
Figure 3:
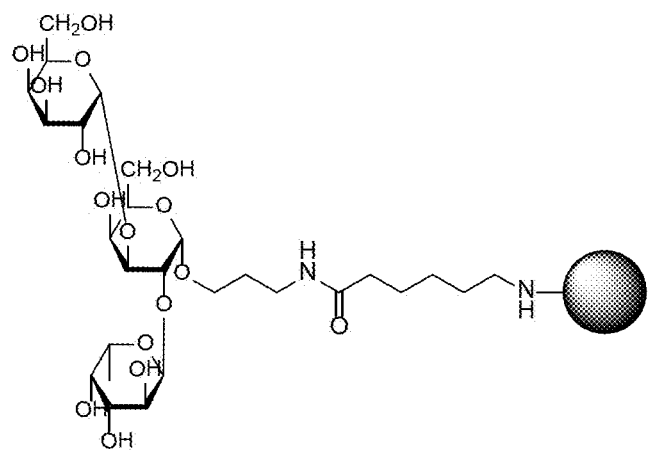
FIG. 3 illustrates a simplified diagram of a preferred embodiment of the invention, illustrating a polymeric particle on which a trisaccharide corresponding to a blood group B epitope is grafted.

In a preferred embodiment, beads of crosslinked cellulose are mixed, on which are grafted ligands which are trisaccharides corresponding to a blood group A epitope (N-acetylgalactosamine (GalNAc)-Galactose(Gal)-Fucose), as illustrated in FIG. 2, and cross-linked cellulose beads on which are grafted ligands which are trisaccharides corresponding to a blood group B epitope, (Galactose-Galactose-Fucose), as illustrated in FIG. 3. The trisaccharides are grafted to the beads with a spacer of formula: (bead)-NH—$C_5H_{10}$—CO—NH—$C_3H_6$-(ligand).

Preparation of the Matrix:

The ligands are chemically immobilized by covalent bonds between the particles and the spacer, and between the spacer and the ligand.

This immobilization may be achieved in a conventional way by the person skilled in the art.

In a preferred embodiment, the particle bears an arm —NH—R1-COOH. Preferably, this is ε-aminocaproic acid (wherein R1 is a pentyl group).

Conventionally, the particle may be activated by using bifunctional reagents such as epichlorhydrin, epibromhydrin, dibromo- and dichloropropanol, dibromobutane, ethylene glycol diglycidylether, butanediol diglycidylether, divinylsulfone, allylglycidylether and allyl bromide. The bifunctional reagent is capable of both reacting with the particles and the arm —NH—R1-COOH. The allyl heterofunctional compounds, such as allyl bromide are preferred bifunctional reagents and give the possibility of obtaining an activated matrix.

For certain solid supports, such as cellulose, composites containing a hydrogel or other materials having hydroxyl groups, it is advantageous to remove the protons from the hydroxyl groups with a hydroxide source, for example, before the reaction with a bifunctional reagent.

The ligands representing antigens of the blood groups A and/or B are then immobilized on the activated particle bearing the arm —NH—R1-COOH via a binder group —NH—R2, wherein R2 is a linear or branched, preferably linear $C_3$-$C_8$ alkyl group. For this, the COOH function of the arm —NH—R1-COOH borne by the particle is reacted with the $NH_2$ function of the ligand $NH_2$—R2-oligosaccharide, by applying a condensation agent of the N-ethoxycarbonyl-2-ethoxy-1,2-dihydroquinoline type (EEDQ).

The person skilled in the art may either graft a ligand representing a group A antigen or a ligand representing a group B antigen, or further both, on the same particle. Preferably, the spacer used is identical. This is particularly advantageous for ensuring equivalent grafting of ligands representing a group A antigen with respect to the ligands representing a group B antigen. The person skilled in the art moreover knows how to adopt suitable conditions, depending on the reactivity of the ligands towards the particles, in order to obtain particles bearing a determined proportion of ligands representing a group A antigen with respect to the ligands representing a group B antigen.

The matrix as a gel is prepared by standard addition of a buffer on the polymeric particles bearing the ligands, as this is known to the person skilled in the art, so as to obtain a matrix as a gel, adapted for affinity chromatography.

Advantageously, the density of ligands, i.e. the amount of ligands (i.e. of oligosaccharides corresponding to a blood group A or B epitope) grafted per volume of matrix, is comprised between about 0.2 and about 0.7 mg/ml of matrix, still preferably between about 0.3 and about 0.4 mg/ml of matrix. Preferably the density of oligosaccharides is of about 0.3 mg/ml of matrix.

According to the invention, this density gives the possibility of drastically decreasing the purification time by affinity chromatography, as compared with a density of 1 mg/ml (for example on a GLYCOSORB ABO® gel from Glycorex Transplantation AB (Sweden), mentioned in application WO2007/077365). The matrix volume may be increased and the flow rate through the chromatography column may be increased. Thus, with a density of ligands of 0.3 mg/ml of matrix (as compared with a density of 1 mg/ml), the duration of the process was divided by 2, which, on an industrial scale represents a remarkable gain. Advantageously, the decrease in the density of ligands also allows a reduction in the cost of the matrix, and thus makes the affinity step on the matrix according to the invention less expensive, contributing to reducing the price cost of the final composition of immunoglobulins. Advantageously, the decrease in the density of ligands is accompanied by preservation of the capability of removing the anti-A and/or anti-B antibodies.

In a preferred embodiment, the polymer particles on which at least one oligosaccharide corresponding to a blood group A epitope is grafted, and the polymeric particles on which at least one oligosaccharide corresponding to a blood group B epitope is grafted, may then be mixed, for example in a proportion from 25/75 to 75/25 (v/v), preferably about 50/50 (v/v).

The polymer particles on which at least one oligosaccharide corresponding to the blood group A epitope is grafted, and the polymeric particles on which at least one oligosaccharide corresponding to a blood group B epitope is grafted, may also, if necessary, be mixed with polymeric particles both bearing at least one oligosaccharide corresponding to a blood group A epitope and at least one oligosaccharide corresponding to a blood group B epitope.

Affinity Chromatography:

The matrix as defined here is useful in affinity chromatography binding anti-A and/or anti-B antibodies.

For this, the matrix may be introduced into a chromatography column. On an industrial scale, the column may contain from 1 to 150 liters, or even 250 to 500 L, if required. In the case of an application at a pilot scale, it is possible to use columns with a height from 1 to 50 cm, the diameter is then adapted to the column height used. The volume of matrix used in the column is adjusted according to the desired residual level of anti-A and/or anti-B antibodies relatively to the initial anti-A and/or anti-B antibody level of the solution. The matrix volume may also be adjusted in order to meet the constraints of an industrial process, notably to be adapted to the volumes of product to be treated.

The anti-A and/or anti-B antibodies present in the liquid preparation of immunoglobulins (or the derivative of blood products) bind to the matrix, and the non-adsorbed product is recovered, depleted in anti-A and/or anti-B antibodies. The liquid preparation of immunoglobulins or the derivative of blood products is poured through the matrix at a rate and under conditions which allow binding of the antibodies with the ligands borne by the matrix.

The matrices may be reused repeatedly, for example up to about 100 times without any degradation. Their regeneration may be achieved by procedures known to the person skilled in the art, for example by treatment with soda (NaOH), for example at 1 M. The reuse after regeneration meets the safety requirements of an industrial process for making drugs, notably the needs for biological decontamination and the removal of product traces which may induce a contamination from batch to batch. By reusing the affinity matrix, it is also advantageously possible to lower the industrial price cost during the manufacturing of immunoglobulins.

The affinity matrix according to the invention is therefore perfectly adapted to industrial use for manufacturing drugs such as immunoglobulins, by allowing robust and sufficient removal of the anti-A and/or anti-B antibodies initially present in the solution, without dramatically increasing the industrial price cost of the final immunoglobulin product.

Purification of Immunoglobulin Products:

Affinity chromatography using the matrix of the invention is particularly advantageous for purifying preparations or compositions of immunoglobulins, by removing the undesirable anti-A and/or anti-B antibodies possibly present in these preparations or compositions, and thus preparing concentrates of immunoglobulins for therapeutic use. By "removing", is meant a substantial reduction in the amount of anti-A and/or anti-B antibodies present, preferably by at least 25%, still preferably by at least 50%, still more preferentially by at least 80 or 90%. The Ig concentrate of the invention obtained after affinity chromatography has respective contents of anti-A and anti-B antibodies (at a dilution of 1/64) compliant with a negative test in the direct Coombs test applied with an initial concentration of IgG of 30 g/L. Preferably, the Ig concentrate of the invention obtained after affinity chromatography comprises an anti-A antibody content which is not greater than 23 ng/mg of IgG, and an anti-B antibody content which is not greater than 20 ng/mg of IgG. Methods for dosage of residual anti-A and anti-B antibodies are notably described in application WO2007/077365. Preferably, a method for dosing anti-A and anti-B antibodies is carried out with flow cytometry, the principle of which is based on the use of human erythrocytes of group A or B, according to the intended specific determination of the titer of the anti-A and anti-B antibodies, applying the detection of a fluorescence signal proportional to the contents of these antibodies. The dosage method by flow cytometry generally uses a standard sample, for example a positive control of immunoglobulins (such as a 1:32 titer of EDQM, ref#07/306; Thorpe et al. 2009, Vox Sang. 97, 160-168), or a monoclonal anti-D antibody concentrate or any other suitable reference product.

The immunoglobulin products essentially contain IgGs. Typically, these IgGs are polyclonal IgGs obtained from blood plasma or from a blood plasma fraction already enriched in Ig.

The Ig concentrates for therapeutic use are at concentrations comprised between 50 and 100 g/L. These concentrates are intended for clinical use and may in particular be injected via an intravenous route. For this purpose, they have to be secured and if necessary, should contain excipients, such as stabilizers, compatible with this clinical use.

The Ig concentrates for therapeutic use may also be administered via a sub-cutaneous route. In this case, the concentration of the products is greater than or equal to 100 g/L, advantageously greater than or equal to 150 g/L.

The Ig concentrates for therapeutic use may also be administered via an intramuscular route.

These Ig concentrates may be obtained in the following way:

a) preparation of an Ig composition, for example by ethanol fractionation and/or by caprylic fractionation and/or by chromatographic separation, b) immunoaffinity chromatography by percolation of the Ig composition on a matrix of the invention, and c) biological safety step, preferably nanofiltration so as to remove contaminating viruses and/or particles.

The Ig composition may be obtained by ethanol fractionation originally developed by Cohn et al (Cohn et al, 1946. J. Am. Chem. Soc. 68, 459; Oncley et al, 1949, J. Am. Chem. Soc. 71, 541), or else by chromatographic separation, as for example described in EP 0 703 922 and WO 99/64462, or further by caprylic fractionation as described by Steinbuch et al. 1969, Arch. Biochem. Biophys. 134(2):279-84). The processes developed by the Applicant in patent applications WO 94/29334 and WO 02/092632 and most particularly the one described in WO 02/092632 are most particularly preferred. In this case, blood plasma or a blood plasma fraction enriched in IgG is subject to caprylic fractionation (prepurification by precipitation of non-immunoglobulin contaminants), a single chromatography on an anion exchanger resin support carried out at an alkaline pH, selective elution of the IgGs in a step with a suitable buffer at a pH comprised between 4 and 7. A viral inactivation treatment may be carried out, for example performed by solvent-detergent, as described by Horowitz in U.S. Pat. No. 4,764,369.

The thereby harvested IgG fraction is already concentrated, but may then undergo additional concentration steps by ultrafiltration and sterilizing filtration.

This concentrate is then subject to an immunoaffinity chromatography step on the matrix of the invention. Preferably, the pH of the preparation of immunoglobulins is adjusted to a pH from about 6 to about 7, preferably of about 6, before the chromatography.

The load of the column is adapted to the sought residual level of anti-A and/or anti-B antibodies. The specificity of such a matrix does not require prior conditioning of the IgG fraction, i.e. any IgG fraction or concentrate obtained by plasma fractionation techniques may be suitable.

The percolation of the concentrate does not involve any elution mechanism. Therefore, regardless of how the IgG concentrate is obtained, it is percolated through the column, optionally by means of a pump. This percolation allows retention of the anti-A and anti-B antibodies. The contact time between the ligands and the Ig preparation is greater than or equal to one minute, advantageously of the order of 2 minutes.

The column may then be washed with water for recovering the IgGs still present in the dead space of the column.

After percolation of the IgG concentrate, an IgG fraction depleted in anti-A and anti-B antibodies is obtained.

The process may comprise, subsequently concentration steps by ultrafiltration and sterilizing filtration.

The chromatography column and the matrix may then be washed and eluted, in order to desorb the retained anti-A and anti-B antibodies.

The example which follows illustrates the present invention without however limiting the scope thereof.

EXAMPLE

Affinity Chromatography (Industrial Scale)

Chromatography Conditions:

A preparation of immunoglobulins, obtained by fractionation according to the process described in application WO2002/092632, comprising 10±2 g/L of IgG is subject, on an industrial scale to an anti-A/anti-B affinity chromatography step conducted on a column comprising a 50/50 mixture (v/v) of crosslinked cellulose beads on which are grafted trisaccharides corresponding to a blood group A epitope (N-acetylgalactosamine (GalNAc)-Galactose(Gal)-Fucose), as illustrated in FIG. 2 (gel designated as "Iso A HyperCel"), and crosslinked cellulose beads on which are grafted trisaccharides corresponding to a blood group B epitope (Galactose-Galactose-Fucose), as illustrated in FIG. 3 (gel designated as "Iso B HyperCel").

The trisaccharides are grafted to the beads through a spacer of formula:

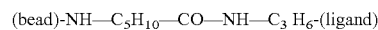

(bead)-NH—C$_5$H$_{10}$—CO—NH—C$_3$ H$_6$-(ligand)

The density of grafted trisaccharides is of 0.3 mg per ml of matrix gel.

In order to check the anti-A and anti-B residual activity, the preparation of immunoglobulins designated as Eluate (a fraction obtained after anion exchange chromatography), for which the pH was adjusted to 6 (±0.05) was passed over a 1 ml column (comprising 0.5 ml of gel Iso A HyperCel+0.5 ml of gel Iso B HyperCel)

Format of the column: D=0.5 cm×5.1 cm (volume of the column (VC)=1 ml).

Contact time: 2 min

Load: 6 g of eluate preparations/mg of A+B ligands, i.e. 180 ml of product per column. After the test, the gel is washed with water (minimum 10 VCs).

The conditions of the different steps of the process are summarized in the table below:

Table of the Steps:

| Step | Solution | Volume |
|---|---|---|
| Sanitization | NaOH 1M (30 min) | 6 VC |
|  | Phosphate 1M pH 8.0 | 4 VC |
| Balance | PPI water | 10 VC |
|  | (Return to neutral pH 5 to 7) |  |
| Binding | Eluate | ±180 ml |
| Non-fractionated collection of the NAF |  |  |
| Washing | NaCl 150 mM + Phosphate 15 mM pH 6.2 | 10 VC |
| Acid elution | Glycine 0.1M pH 3 | 6 VC |
| Basic elution | Glycine 0.1M pH 11 | 6 VC |

VC: column volume;
NAF: Non-adsorbed fraction
A single non-adsorbed fraction (NAF) was collected.

Dosage Tests:

The yield was determined by dosing the IgGs in the nonadsorbed fraction, after washing and percolation. The anti-A and anti-B residual activity corresponding to the percentage of anti-A and anti-B isoagglutinins present in the final preparation with respect to their concentration before the affinity chromatography step, was measured by flow cytometry (a more sensitive and accurate technique than that of dilutions as required by the European Pharmacopeia), according to the technique described below. Red cells of groups A and B were collected on EDTA and washed twice in a 0.9% NaCl solution (centrifugation at 1,730 g for 5 mins between both washings). $2 \cdot 10^6$ red cells were distributed on a microtitration plate and 50 μL of standard positive control (1:32 EDQM, ref#07/306; Thorpe et al. 2009) or samples diluted to a working concentration (PBS pH 7.4, 1% BSA) were added. The plates were incubated for 2h at 37° C. with stirring. After washing, human anti-IgG goat F(ab')$^2$ antibody (Fc specific) (Beckman Coulter) marked with phycoerythrin (PE) was used diluted to 1/20 in PBS-BSA. The plates were incubated for 30 mins at room temperature and away from light.

After washing, each pellet was resuspended in 200 μL of PBS-BSA, and read out with a flow cytometer (Beckman Coulter Cytomics FC 500).

The mean fluorescence intensity (MFI) of the positive control was reported versus the concentration of IgG (standard curve) for concentrations ranging from 0.23 g/L to 30 g/L. The results are expressed as the ratio between the slope of the sample and the slope of the positive standard. The equation of the standard curve is y=ax+b; wherein "a" is the value of the slope of the standard curve and "b" is the zero point corresponding to the background noise of the test. As the equation of the sample is y'=a'x+b, and by using the known values of MFI of the sample (y') and the concentration of IgG (x'), the ratio of the slopes was calculated as being [(MFIb)/[IgG concentration]]/a.

Results:

The obtained IgG yield and anti-A and anti-B residual activity are shown in the table below:

Table of the Results:

|  | Vol (mL) | Conc. (g/L) IgG | Amount (g) IgG | Load g/mg ligands A + B gel | Cytometer: Anti-A IgG calculation residual act. | Cytometer: Anti-B IgG calculation residual act. |
| --- | --- | --- | --- | --- | --- | --- |
| Start | 180.0 | 11.60 | 2.1 | 6.8 | 5.14 | 3.44 |
| FNA | 183.8 | 11.10 | 2.0 |  | 0.60 | 0.29 |
| Washing + E + R | 18.8 | 1.20 | 0.0 |  | 12% | 8% |

The results of this table show an IgG yield of 98% in the nonadsorbed fraction, which proves that the affinity support has good specificity towards anti-A and anti-B isoagglutinins.

The results of this table also show a substantial reduction in the anti-A and anti-B residual activity, which are 12% and 8% respectively. The thereby obtained product is then compliant (at the dilution of 1/64) with a negative result in the direct Coombs test applied with an initial concentration of IgG at 30 g/L.

The invention claimed is:

1. An affinity chromatography matrix, in form of a gel, comprising polymeric particles on which at least one oligosaccharide corresponding to a blood group A and/or group B epitope is grafted via a spacer, wherein:
   the density of oligosaccharides is from about 0.3 to about 0.4 mg/ml of the matrix and
   said spacer has a formula provided by

NH—R1—CO—NH—R2-     (I), wherein R1 is a $C_5$ alkyl group, R2 is a $C_3$ alkyl group, and said spacer is bound through its amine function to the particle.

2. The matrix according to claim 1, comprising (i) polymeric particles on which at least one oligosaccharide corresponding to a blood group A epitope is grafted, and/or (ii) polymeric particles on which at least one oligosaccharide corresponding to a blood group B epitope is grafted.

3. The matrix according to claim 2, comprising (i) polymeric particles on which at least one oligosaccharide corresponding to a blood group A epitope is grafted, and (ii) polymeric particles on which at least one oligosaccharide corresponding to a blood group B epitope is grafted.

4. The matrix according to claim 1, comprising polymeric particles on which both at least one oligosaccharide corresponding to a blood group A epitope and at least one oligosaccharide corresponding to a blood group B epitope, are grafted.

5. The matrix according to claim 1, comprising a mixture of (i) polymeric particles on which at least one oligosaccharide corresponding to a blood group A epitope is grafted, (ii) polymeric particles on which at least one oligosaccharide corresponding to a blood group B epitope is grafted, and (iii) polymeric particles on which both at least one oligosaccharide corresponding to a blood group A epitope, and at least one oligosaccharide corresponding to a blood group B epitope, are grafted.

6. The matrix according to claim 1, wherein the oligosaccharide corresponding to a blood group A epitope and/or the oligosaccharide corresponding to a blood group B epitope is a trisaccharide.

7. The matrix according to claim 6, wherein the oligosaccharide corresponding to a blood group A epitope is a trisaccharide N-acetylgalactosamine (GalNAc)-Galactose (Gal)-Fucose.

8. The matrix according to claim 6, wherein the oligosaccharide corresponding to a blood group B epitope is an oligosaccharide Galactose-Galactose-Fucose.

9. The matrix according to claim 3, wherein the polymeric particles on which at least one oligosaccharide corresponding to a blood group A epitope is grafted, and the polymeric particles on which at least one oligosaccharide corresponding to a blood group B epitope is grafted, are mixed in a proportion of 25/75 to 75/25 (v/v), preferably about 50/50 (v/v).

10. The matrix according to claim 1, wherein the polymer is a cross-linked polymer.

11. The matrix according to claim 10, wherein the polymer is cellulose.

12. A method of using the matrix as defined in claim 1, in an affinity chromatography binding anti-A and/or anti-B antibodies.

13. The method of using the matrix according to claim 12, for producing on an industrial scale immunoglobulins G (IgG) for therapeutic use.

14. A process for preparing a concentrate of immunoglobulins G (IgG) for therapeutic use, comprising obtaining an Ig composition from blood plasma, by ethanol fractionation and/or caprylic fractionation and/or chromatographic separation, and subjecting the Ig composition to affinity chromatography using the matrix of claim 1 to remove the anti-A and/or anti-B antibodies from the Ig composition.

15. The matrix according to claim 1, wherein the density of oligosaccharides is about 0.3 mg/ml of matrix.

16. The matrix according to claim 11, wherein the particles are porous, cross-linked cellulose beads.

17. An affinity chromatography matrix, in form of a gel, comprising polymeric particles on which at least one oligosaccharide corresponding to a blood group A and/or group B epitope is grafted via a spacer, wherein:

the at least one oligosaccharide is a trisaccharide;

the density of oligosaccharides is from about 0.3 to about 0.4 mg/ml of the matrix;

said spacer has a formula provided by

NH—R1-CO—NH—R2-                       (I), wherein R1 is a $C_5$ alkyl group, R2 is a $C_3$ alkyl group, and said spacer is bound through its amine function to the particle; and the particles are porous cross-linked cellulose beads.

* * * * *